(12) United States Patent
Neoh

(10) Patent No.: US 8,882,681 B2
(45) Date of Patent: Nov. 11, 2014

(54) THROUGH-CRADLE SOFT TISSUE BIOPSY DEVICE

(75) Inventor: Wen Hong Neoh, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 230 days.

(21) Appl. No.: 13/172,187

(22) Filed: Jun. 29, 2011

(65) Prior Publication Data
US 2013/0006143 A1   Jan. 3, 2013

(51) Int. Cl.
  A61B 10/00   (2006.01)
  A61B 10/02   (2006.01)
  A61B 10/04   (2006.01)

(52) U.S. Cl.
  CPC ..... *A61B 10/0275* (2013.01); *A61B 2010/0208* (2013.01); *A61B 2010/045* (2013.01)
  USPC ........................................... 600/567; 600/566

(58) Field of Classification Search
  CPC ........... A61B 10/0233; A61B 10/0266; A61B 10/0275; A61B 10/0283
  USPC ................................................. 600/566, 567
  See application file for complete search history.

(56) References Cited

U.S. PATENT DOCUMENTS

| | | | | |
|---|---|---|---|---|
| 3,605,721 A | * | 9/1971 | Hallac | 600/567 |
| 4,099,518 A | | 7/1978 | Baylis et al. | |
| 4,640,296 A | * | 2/1987 | Schnepp-Pesch et al. | 600/567 |
| 5,394,887 A | * | 3/1995 | Haaga | 600/567 |
| 5,449,001 A | * | 9/1995 | Terwilliger | 600/567 |
| 5,744,360 A | * | 4/1998 | Hu et al. | 435/366 |
| 5,830,153 A | * | 11/1998 | Kass | 600/567 |
| 5,921,943 A | * | 7/1999 | Kass | 600/567 |
| 5,944,673 A | * | 8/1999 | Gregoire et al. | 600/564 |
| 5,964,716 A | * | 10/1999 | Gregoire et al. | 600/564 |
| 6,027,458 A | * | 2/2000 | Janssens | 600/567 |
| 6,142,955 A | | 11/2000 | Farascioni et al. | |
| 6,162,203 A | | 12/2000 | Haaga | |
| 6,261,243 B1 | * | 7/2001 | Burney et al. | 600/564 |
| 6,497,706 B1 | * | 12/2002 | Burbank et al. | 606/45 |
| 6,572,563 B2 | | 6/2003 | Ouchi | |
| 7,022,085 B2 | | 4/2006 | Cooke et al. | |
| 7,063,672 B2 | | 6/2006 | Schramm | |
| 7,066,893 B2 | * | 6/2006 | Hibner et al. | 600/566 |
| 7,156,815 B2 | | 1/2007 | Leigh et al. | |
| 7,226,424 B2 | | 6/2007 | Ritchart et al. | |
| 7,416,533 B2 | * | 8/2008 | Gellman et al. | 600/562 |
| 7,481,775 B2 | | 1/2009 | Weikel, Jr. et al. | |
| 7,510,535 B2 | * | 3/2009 | Hibner et al. | 600/566 |
| 7,717,861 B2 | | 5/2010 | Weikel et al. | |
| 7,766,843 B2 | | 8/2010 | Voegele | |
| 7,828,746 B2 | | 11/2010 | Teague | |
| 7,841,990 B2 | | 11/2010 | Mark et al. | |
| 7,914,463 B2 | | 3/2011 | Tarter et al. | |

(Continued)

Primary Examiner — Sean Dougherty
Assistant Examiner — Michael C Stout
(74) Attorney, Agent, or Firm — Woodard, Emhardt, Moriarty, McNett & Henry LLP

(57) ABSTRACT

Among other things, there is disclosed a biopsy needle having a cutting cannula axially slidable over an inner stylet. The inner stylet has a proximal portion connected to a distal portion that includes first and second spaced-apart struts. The distal portion has a tissue penetrating tip and the stylet defines a sample-containment space between the struts having first and second radially opposed lateral openings thereto. The sample-containment space of the stylet readily accepts tissue through either of the lateral openings such that a near full core of tissue can be sampled.

17 Claims, 4 Drawing Sheets

(56) References Cited

U.S. PATENT DOCUMENTS

| | | | |
|---|---|---|---|
| 7,946,998 B2* | 5/2011 | Gellman et al. | 600/562 |
| 8,251,917 B2* | 8/2012 | Almazan | 600/566 |
| 8,262,585 B2* | 9/2012 | Thompson et al. | 600/564 |
| 2002/0029007 A1* | 3/2002 | Bryan et al. | 600/565 |
| 2003/0212343 A1 | 11/2003 | Plishka | |
| 2003/0229293 A1* | 12/2003 | Hibner et al. | 600/567 |
| 2005/0124914 A1 | 6/2005 | Dicarlo et al. | |
| 2006/0074346 A1* | 4/2006 | Hibner | 600/566 |
| 2006/0089563 A1 | 4/2006 | McAlister et al. | |
| 2006/0241516 A1* | 10/2006 | Hibner et al. | 600/566 |
| 2006/0258953 A1 | 11/2006 | Lee | |
| 2007/0016099 A1 | 1/2007 | Chin et al. | |
| 2007/0239064 A1* | 10/2007 | Cicenas et al. | 600/566 |
| 2008/0114265 A1* | 5/2008 | Tarter et al. | 600/567 |
| 2008/0281224 A1 | 11/2008 | Johnson | |
| 2008/0287825 A1 | 11/2008 | Cooke | |
| 2008/0300506 A1* | 12/2008 | McIntyre | 600/566 |
| 2008/0300507 A1 | 12/2008 | Figueredo et al. | |
| 2010/0069788 A1 | 3/2010 | Dell'Oca et al. | |
| 2010/0076342 A1 | 3/2010 | Miller | |
| 2010/0160824 A1 | 6/2010 | Parihar et al. | |
| 2010/0280408 A1 | 11/2010 | Rusnak | |
| 2010/0305470 A1 | 12/2010 | Ireland | |
| 2011/0004120 A1 | 1/2011 | Drubetsky | |
| 2011/0021949 A1* | 1/2011 | McAlister et al. | 600/567 |
| 2011/0098596 A1* | 4/2011 | Ozturk et al. | 600/566 |
| 2011/0137202 A1* | 6/2011 | Gim et al. | 600/567 |
| 2012/0022397 A1* | 1/2012 | Jarial | 600/567 |

* cited by examiner

THROUGH-CRADLE SOFT TISSUE BIOPSY DEVICE

This disclosure concerns devices for obtaining a tissue sample in biopsy. More particularly, but not exclusively, this disclosure concerns devices which obtain a full or near-full core tissue sample while maintaining rigidity and ease of use.

BACKGROUND

It is often desirable to perform a biopsy to sample selected tissue from a patient for medical evaluation. For example, biopsies can be useful in diagnosing various forms of cancer and other diseases affecting a localized area of tissue. Traditional notched stylet biopsy needles comprise an inner stylet having a lateral-facing specimen notch slidably disposed within an outer cutting cannula. In typical use, the inner stylet is inserted into tissue to be sampled and, after a tissue specimen has prolapsed into the specimen notch, the outer cutting cannula is fired over the stylet. The sharpened distal end of the cutting cannula severs the captured tissue specimen from the surrounding tissue and holds it within the notch of the stylet. Commercially-available notched stylet biopsy needles often come with different throw lengths, such as 10 mm or 20 mm, where the throw length refers to a longitudinal length of the notch exposed before the cutting cannula is fired, and consequently also refers to the approximate length of the sample obtained.

In traditional notched-stylet biopsy needles, the inner circumference of the cutting cannula is typically circular, and the cross section of the specimen notch of the stylet is either semi-circular or C-shaped. Because of the cross-sectional area taken up by the stylet, the amount of tissue captured in the notch is necessarily significantly less than the full cylindrical volume, or "full core," defined by the outer cannula. Typically, the tissue sample obtained is characterized by a cross section that is asymmetrically truncated relative to the full circular core of the cutting cannula. If the notch is not facing toward the tissue of interest, than an incorrect sample may be initially obtained. Thus, in order to obtain a suitable amount of tissue for medical evaluation, it can be necessary to take multiple biopsy samples or to use needles with longer throw lengths.

Moreover, the performance of some notched stylets can suffer due to inadequate strength or stability. For example, commercially-available notched stylets can have a tendency to bend or deflect as they penetrate tissue, which can adversely affect the quality of the sample taken. Because increasing the throw length (i.e. extending the thinner notched portion) generally leads to a decrease in the rigidity of the stylet, the risk of sample inadequacy or unsuitability due to unwanted deflection of the stylet generally increases when longer throw lengths are used. Further, increasing the amount of tissue obtained by increasing depth of the notch is not indicated for traditional needles for several reasons. If the notch depth is to be increased, either the overall size of the stylet and its cannula must be increased, or more of the stylet must be removed to form the notch, or both. However, increasing overall size can increase the discomfort for the patient and difficulty in inserting the needle through potentially dense tissue. Removing more of the stylet results in a stylet more prone to the bending or deflection noted above.

While existing partial core products can be effectively used, there is a need for a biopsy device that addresses existing problems and can obtain a tissue sample having a cross section that is larger and more symmetrical relative to the overall cross section of the device, while being easier and more inexpensive to manufacture than existing "full core" needles and being as or more reliable than existing partial core needles.

SUMMARY

Among other things, there is shown and described a biopsy needle device of the type including an outer cannula having a tissue cutting distal end and a stylet located within the cannula. The stylet and the cannula are axially movable with respect to each other. The stylet is constructed to have a tissue-penetrating distal portion with a pair of spaced apart elongated members or struts, to define a sample-containment space having first and second relatively large, radially-opposed openings thereto such that, during use, tissue can prolapse into the sample-containment space via either or both of the openings.

There is also shown and described a biopsy needle having an inner stylet wherein the sample containment space of the stylet is defined by first and second spaced apart elongated members or struts which define a longitudinal plane, and the distal tissue penetrating tip of the stylet is located on the longitudinal plane so as to reduce the tendency for the stylet to deflect when inserted through soft tissue.

There is also shown and described a biopsy needle having an inner stylet that defines a sample containment space wherein a radial dimension of the sample containment space expands when the stylet is extended from the end of the cutting cannula and contracts the cutting cannula is extended over the stylet.

In some embodiments, a biopsy needle includes an external tubular member (or cannula) having an internal lumen and a sharpened distal end and an internal member (or stylet) defining a central longitudinal axis and having a proximal portion connected to a distal portion. The internal member's distal portion has first and second spaced apart struts and a tissue penetrating tip, with the internal member defining a sample-containment space located between said first and second spaced apart struts and having first and second radially-opposed lateral openings thereto.

The internal member is slidably positioned within the lumen of the external member between a first relative position in which the sample-containment space and lateral openings are at least partially extended from the external member, and a second relative position in which the sample-containment space and lateral openings are entirely within that lumen.

Particular embodiments may have the first and second struts each with a respective concave interior surface, and those concave interior surfaces may be uniform along the respective lengths of the struts, each forming a portion of a cylinder centered on the central longitudinal axis. The tissue penetrating tip is in a longitudinal plane defined by said first and second struts or their respective center lines in some examples, and in others is aligned with the central longitudinal axis. The first and second openings may have approximately the same length measured along the longitudinal axis, or in other embodiments the first opening can have a larger length measured along the longitudinal axis than the second opening. The first opening may subtend an arc of the perimeter of said inner member that is different from that subtended by the second opening, and may be more than 180 degrees, e.g. approximately 200 degrees. Alternatively, each of the respective openings can circumferentially extend between 90 and 180 degrees about the longitudinal axis of the inner member. A line connecting or a plane including the respective middles of the first and second struts may be offset from the longitudinal axis.

Embodiments may have a distal portion of the inner member that includes first and second end surfaces bounding the containment space, and the end surfaces contact each of the struts and can be oblique to the longitudinal axis. Such end surfaces can be substantially planar from top to bottom, i.e. through an entire diameter of the inner member, and may point toward each other. The first and second struts have respective internal surfaces facing the containment space and opposed external surfaces, with the internal surfaces having a cylindrical curvature centered on the longitudinal axis. The inner member is a tubular (e.g. hollow) member having an inner diameter in some embodiments, and the cylindrical curvature of the internal surface is the inner diameter of the tubular member. In other embodiments, the inner member is a non-hollow solid member, such that the sample-containment space faces or is adjacent to the solid middle of the inner member. The inner member's external surface may also have a cylindrical curvature centered on the longitudinal axis. That cylindrical curvature of the external surface may have an outer diameter approximately the same as that of the external member's lumen. Some embodiments of the inner member have a distal portion with a distal end sharpened so as to have a profile that is generally symmetric relative to a longitudinal plane defined by the first and second struts.

Embodiments of the external member define an inner circumference and an outer circumference and may have first and second cutting edges for cutting across the first and second side openings of the containment space of the inner member. Such cutting edges can be axially aligned with the outer circumference of the external member, and/or axially aligned with the inner circumference of the external member.

Biopsy needles disclosed herein can include an inner stylet defining a sample-containing space and being within an outer cutting cannula that is axially slidable over the inner stylet to sever a sample of tissue captured in the sample-containment space. A proximal portion of the inner stylet is connected to a tissue-penetrating distal portion of the inner stylet via a plurality of elongated struts, with the struts defining spaced apart walls of the sample-containing space. The walls of the sample-containing space are spaced apart an equal distance along the longitudinal length of the sample-containment space.

Methods disclosed herein include methods of taking a percutaneous biopsy. For example, a biopsy needle may be provided having an inner member defining a sample-containment space and being within an outer cutting cannula that is axially slidable over the inner member so as to sever a sample of tissue captured in a sample-containment space of the inner member. A proximal portion of the inner member is connected to a tissue-penetrating portion of the inner member via first and second elongated struts that define spaced apart walls of the sample-containment space. The needle is inserted through the skin to a predetermined location, and the sample-containment space is exposed by sliding the inner member and the outer cutting cannula relative to each other, allowing tissue to prolapse into the sample-containment space from one or both of two different sides of the struts. The outer cutting cannula and the inner member are slid relative to each other to sever the tissue which has prolapsed into the sample-containment space, and the needle is withdrawn with the tissue in the sample-containment space. The sample-containment space can be exposed by advancing the inner member distally into the tissue to be sampled.

Using needles as disclosed, the clinician can aim for the tissue of interest itself and not necessarily to one side or edge of it. Embodiments permit the user to insert the needle to the middle of tissue of interest, so that such tissue may enter the needle from one or more directions. There is less chance of inserting a needle and having a biopsy opening facing the wrong way, or of including tissue not of interest in the biopsy opening. These and other embodiments present biopsy needles that have structural rigidity and/or can take a larger sample of tissue compared to existing partial-core biopsy needles.

DESCRIPTION OF THE ILLUSTRATED EMBODIMENTS

Figure 1A:
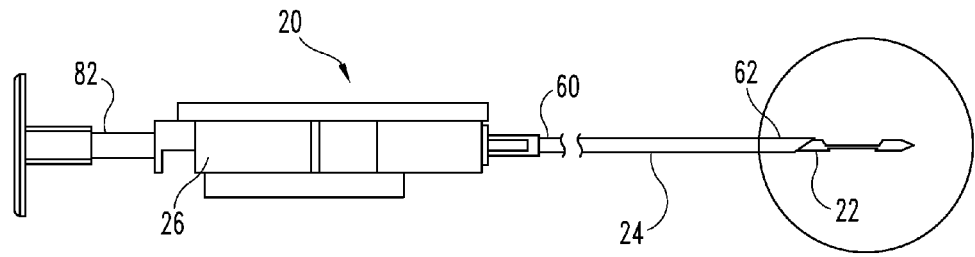
FIG. 1A is a side elevational view of an embodiment of a biopsy needle according to the present disclosure.

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates.

Referring to the drawings, there are shown embodiments of a biopsy needle 20 that can be used to sample soft tissue, among other things. Needle 20 includes an internal member or stylet 22, an external member or cannula 24, and a handle 26. As will be discussed further below, an operator can insert stylet 22 and external member 24 into a patient and can move stylet 22 and external member 24 with respect to each other by operating handle 26. The selective relative movement of those parts obtain a sample of tissue from within the patient.

Figure 1B:
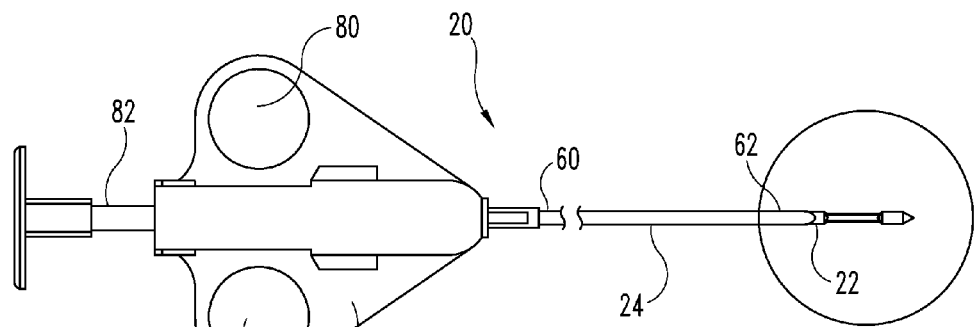
FIG. 1B is a top plan view of the embodiment of FIG. 1A.

Stylet 22 is an elongated member having a distal portion 30 and a proximal portion 31, with proximal portion 31 connected to handle 26. Stylet 22 extends through cannula 24 and has a length sufficient to reach from handle 26 to tissue of interest within a patient. Distal portion 30 includes an end 32 that is sharpened to a tissue-penetrating tip 33. In particular embodiments, tip 33 is sharpened to such a degree that it can easily penetrate tissue such as skin, subdermal tissue, muscle tissue and/or organ tissue, and in particular embodiments tip 33 comes to or approximately to a sharp point 33a. In the embodiment of FIG. 1, point 33a is aligned with the central longitudinal axis of member 22. In other embodiments (e.g. FIGS. 5 and 7), point 33a is aligned with the plane defined by the parallel axes or centers of struts 36, 38.

In the illustrated embodiment, both distal portion 30 and proximal portion 31 are a portion of the same cylindrical piece of material. Accordingly, in such an embodiment both portions 30 and 31 have the same or approximately the same outer shape and diameter throughout. In other embodiments, a distal portion 30 may be separately fabricated and joined to a proximal portion 31 of a different size, shape or configuration. Distal portion 30 has a uniform shape and size in the illustrated embodiment, for example a circular solid cylinder of constant outer diameter, or a circular tube having a constant outer diameter and a constant inner diameter around a lumen 39 or hollow with a constant wall thickness between the outer and inner diameters. As will be described further, inner member 22 may be fashioned from a solid rod or cylinder, from a hollow tube, or from other pieces in the embodiments or with the features described below.

Figure 2:
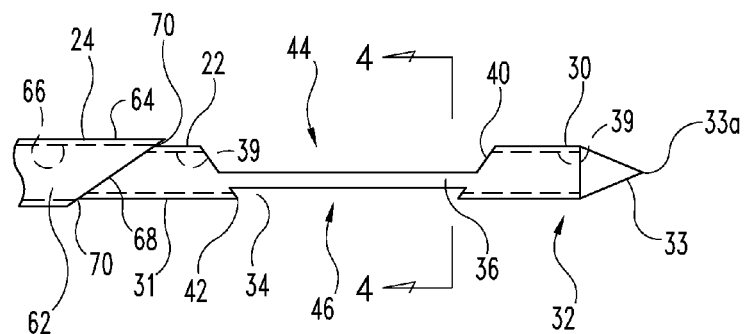
FIG. 2 is a close-up view of the distal portion of the embodiment of FIG. 1B.
Figure 2A:
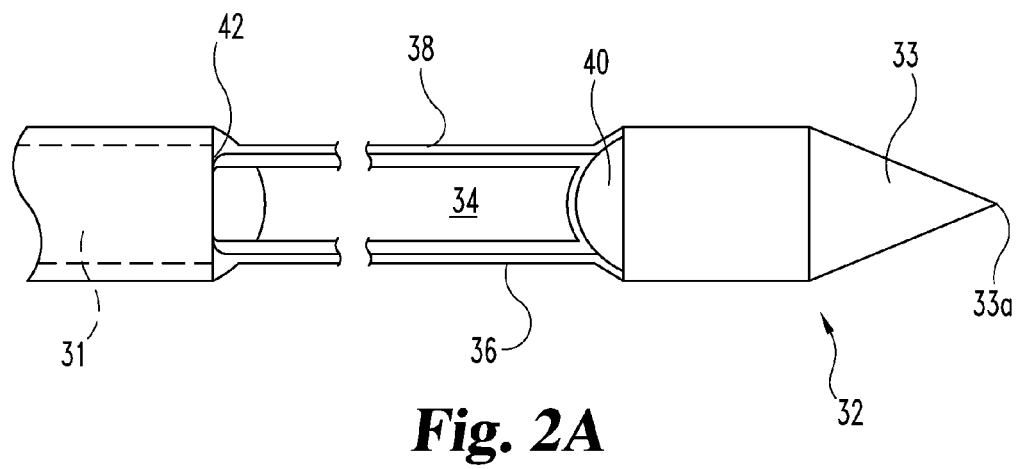
FIG. 2A is a top plan view of the embodiment in FIG. 2.
Figure 3:
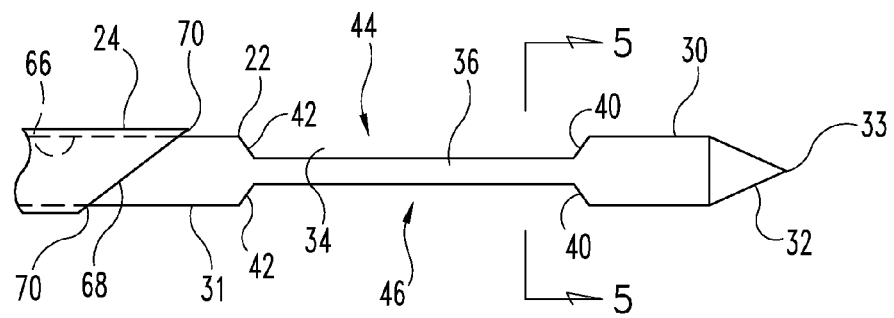
FIG. 3 is a close-up view similar to that of FIG. 2 of a distal portion of an embodiment of a biopsy needle.

Distal portion 30 includes a sample-containment space or tissue cradle 34 defined between a pair of spaced-apart elongated members or struts 36 and 38 and end surfaces 40 and 42. Space 34 may be thought of in this embodiment as being the space within the outer diameter of stylet 22 extended 360 degrees around the longitudinal axis of stylet 22 and between end surfaces 40, 42 and struts 36, 38. Space 34 has two lateral openings 44, 46 (i.e. directed substantially perpendicular to the longitudinal axis of stylet 22), with opening 44 being to one side of the longitudinal axis of stylet 22 and between edges of struts 36, 38, and opening 46 being to the other side of that longitudinal axis and between edges of struts 36, 38. The embodiment shown in FIG. 2 includes openings 44, 46 that are generally radially opposed and symmetric along their longitudinal lengths and circumferentially, with surfaces 40 and 42 each in a respective plane non-parallel to each other. Surfaces 40 and 42 each have respective portions on either side of struts 36 or 38. The embodiment illustrated in FIG. 3 shows two surfaces 40 at a distal end of struts 36, 38, and two surfaces 42 at a proximal end of struts 36, 38. In this embodiment, surfaces 40 are obliquely angled with respect to the central longitudinal axis of stylet 22 and each other, and extensions of their respective planes meet at the central longitudinal axis of stylet 22, and the same is true for surfaces 42. In particular, surfaces 40 and 42 can be angled inward toward each other and the central longitudinal axis of stylet 22, as seen in the examples of FIGS. 2 and 3, so that opening 44 is substantially longer (i.e. the dimension between surfaces 40 and 42) overall than opening 46. It will be seen from the example of FIG. 2 that opening 44 at or adjacent to struts 36, 38 may be wider (i.e. the dimension between struts 36 and 38) than opening 46 at or adjacent struts 36, 38. In other embodiments (e.g. FIG. 3) openings 44 and 46 may be substantially equal in length and/or width, for instance if struts 36, 38 are diametrically opposite each other, and/or if one or more of surfaces 40 and 42 are substantially perpendicular to struts 36, 38 and/or to the central longitudinal axis of stylet 22.

Figure 7:
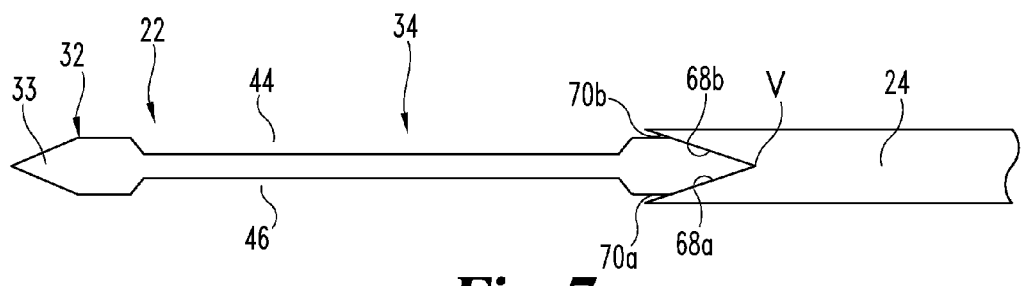
FIG. 7 is a close-up view of a distal portion of an embodiment similar to that of FIG. 3.

Struts 36, 38 each lie along respective axes that are parallel to the longitudinal axis of stylet 22 in the illustrated embodiments. In the embodiment of FIG. 2, struts 36, 38 are generally opposed to each other, but a line or plane P connecting the centers of struts 36, 38 is offset from the central longitudinal axis of stylet 22 (e.g. FIG. 4). That offset condition generates the difference in width of openings 44 and 46 noted above. As indicated in FIGS. 5 and 7, struts 36, 38 may be radially opposed to each other and symmetric about the longitudinal axis of stylet 22 (i.e. a line or plane through the centers of struts 36, 38 in that case intersects with or includes the central longitudinal axis of stylet 22).

Each strut 36, 38 also has a respective inward-facing surface 48a and 48b, and a respective outward-facing surface 50a and 50b. Outer surfaces 50a and 50b of struts 36, 38 are continuous with the outer circumference of the rest of stylet 22 (and thus convex) in the illustrated embodiment, as struts 36, 38 and the rest of stylet 22 are monolithic. Interior surfaces 48a, 48b of struts 36, 38 are concave in the illustrated embodiments and the radial thickness of struts 36, 38 is generally uniform along their longitudinal length and across their height H. Surfaces 50a and 50b, as indicated above, are coextensive with and may be continuations of a uniform outer surface of stylet 22. In embodiments in which stylet 22 is a tubular hollow member, surfaces 48a and 48b may be part of the original inner lumen of the tube. In other embodiments, surfaces 48a and 48b are formed with the rest of space 34, and may be substantially planar, if not concave. In embodiments in which inner surfaces 48a, 48b of one or both of struts 36, 38 are substantially planar, given the convex or cylindrical exterior surface 50a, 50b of struts 36, 38 in the illustrated embodiments such strut(s) will be thicker at a midsection than at the edges. Such a configuration may provide even more resistance to bending forces affecting stylet 22. Struts 36, 38 not only bound at least a portion of space 34, but they also provide rigidity to distal portion 30 of stylet 22. Two struts 36, 38 on either side of a longitudinal axis help minimize or eliminate bending or deflection of stylet 22 as its distal end 32 penetrates through soft tissue.

Figure 4:
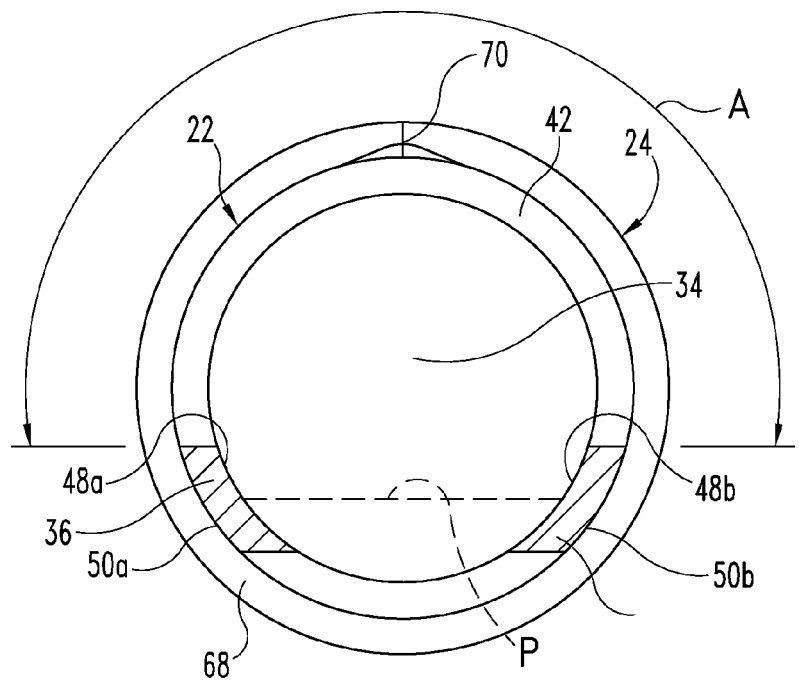
FIG. 4 is a cross-sectional view of the embodiment shown in FIG. 2 taken along the lines 4-4 indicated in FIG. 2.
Figure 5:
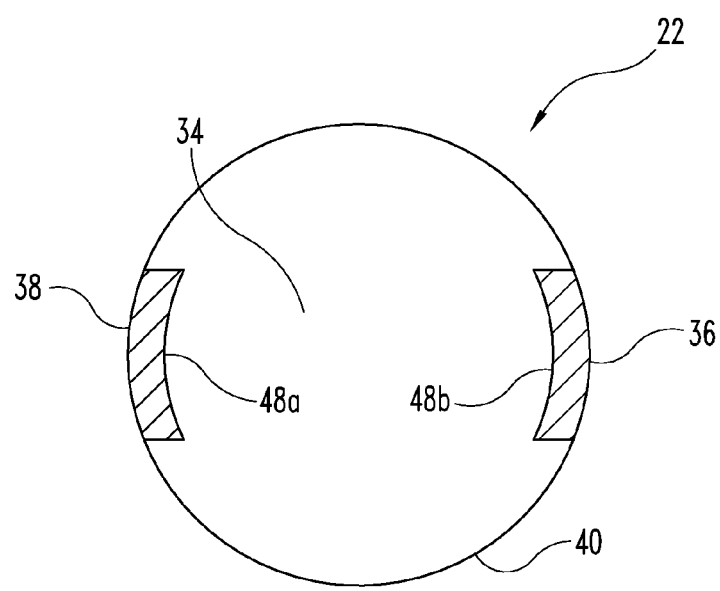
FIG. 5 is a cross-sectional view of the embodiment shown in FIG. 3 taken along the lines 5-5 indicated in FIG. 3.

Struts 36, 38 are shown in FIGS. 2 and 4 positioned so that they form a plane P offset from the central longitudinal axis of stylet 22. Opening 44, measured along an arc A between the upper surfaces of struts 36, 38, extends greater than 180 degrees about the longitudinal axis of stylet 22 (e.g. about 200 degrees or more) in the embodiment of FIG. 4. Opening 46 in that embodiment is smaller in arc (measured between the lower surfaces of struts 36, 38), e.g. about 70-90 degrees of arc around the central longitudinal axis of stylet 22. The embodiment of FIG. 5 shows arcs for openings 44 and 46 that are substantially the same or identical, e.g. about 100-130 degrees measured around the central longitudinal axis of stylet 22, or in a particular embodiment about 120 degrees of arc each.

The illustrated embodiment of external member 24 is a tubular member, or cannula, having a proximal portion 60 which is connected to handle 26 and a distal portion 62 that terminates in a sharpened distal end 64. A central lumen 66 extends through the entirety of cannula 24 to accommodate stylet 22, and in the illustrated embodiment is shaped to match the outer profile of stylet 22. In the embodiment of FIG. 2, both the exterior of stylet 22 and lumen 66 are circular in cross section, but it will be understood that they could be in other shapes or configurations, such as oval or square, in other embodiments. As explained further below, stylet 22 and cannula 24 have a close and slidable fit, allowing them to be easily moved with respect to each other as a user operates handle 26.

Distal end 64 of cannula 24 is sharpened, in one example, by grinding or cutting a surface 68 that is planar and oblique to the longitudinal axis of cannula 24, so as to form at least one cutting edge 70 that can easily penetrate tissue such as skin, subdermal tissue, muscle tissue and/or organ tissue. By forming an oblique surface 68 through cannula 24, edges 70 are formed along at least the relatively proximal portion of the meeting between surface 68 and lumen 66, and along at least the relatively distal portion of the meeting between surface 68 and the outer perimeter or surface of cannula 24. For example, for cutting across opening 44, cutting edge 70 is formed at the intersection of the planar end surface 68 and the outer circumference of cannula 24, and for cutting across opening 46, a cutting edge 70 is formed at the intersection of the planar end surface 68 and the inner circumference of cannula 24. In the example of FIG. 2, the entire distal end 64 of cannula member 24 is ground to about a 45 degree angle to the longitudinal axis to form surface 68 and the cutting edge(s) 70 corresponding to respective openings 44, 46. Such multiple cutting edges 70 are beneficial insofar as there are multiple openings 44, 46 that allow tissue into space 34. They provide respective cuts along openings 44, 46, and can assist in forcing or guiding tissue into space 34 as cannula 24 travels along stylet 22.

Figure 6:
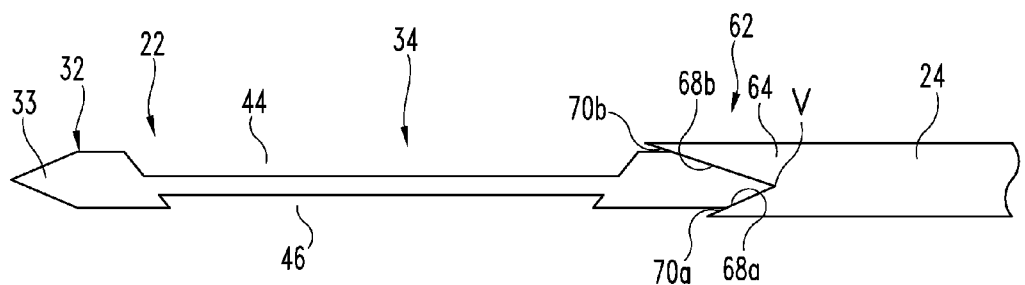
FIG. 6 is a close-up view of a distal portion of an embodiment similar to that of FIG. 2.

As another example, the embodiments in FIGS. 6 and 7 indicate two cuts are made in the end 64 of cannula 24 to create intersecting surfaces 68a and 68b. Accordingly, edge (s) 70a are at the intersections of surface 68a with the outer and/or inner diameters of cannula 24, and edge(s) 70b are at the intersections of surface 68b with those outer and/or inner diameters. FIG. 7 shows surfaces 68a and 68b of approximately equal length or extent along the longitudinal axis, meeting at side points or vertices V (only one of which is seen in the side view of FIG. 7) such that a line connecting those side points intersects the central longitudinal axis of cannula 24. Surfaces 68a and 68b in that configuration may each be considered a major cutting surface. FIG. 6 shows surfaces 68a and 68b of unequal length or extent along the longitudinal axis, meeting at side points or vertices V (only one of which is seen in the side view of FIG. 7) such that a line connecting those side points does not intersect the central longitudinal axis of cannula 24. The tip of surface 68b is longitudinally more distal in such an embodiment than the tip of surface 68a. Surfaces 68a and 68b in that configuration may be respectively considered a minor cutting surface and a major cutting surface with respective edges 70a and 70b. In such a case, where opening 44 is wider or larger in arc than opening 46, a major (longer or further-forward) cutting surface of cannula 24 may be associated with opening 44 of stylet 22, and a minor (shorter or more-rearward) cutting surface may be associated with opening 46. In the embodiments of FIGS. 6 and 7, each cutting edge 68a, 68b comes to a forward point that is generally centered with respect to the respective openings 42, 44.

In these examples, sharpened distal end 62 of cannula 24 has two distinct end surfaces generally defining respective planes at oblique angles to the longitudinal axis of cannula 24. As a result, cutting edges are formed at the intersection of the respective end surfaces and the outer circumference of cannula 24, with each cutting edge coming to a forward point that is generally centered with respect to the respective openings 44, 46 of stylet 22. Accordingly, there is a particular cannula cutting edge associated with each respective stylet opening. When cannula 24 is fired, as described below, the respective edges move over or across their respective openings. The cannula end surfaces may be symmetrical and/or meet at a pair of V-shaped notches, which may be aligned with the longitudinal axes of struts 36, 38. It is to be understood that various types of stylet 22 and cannula 24 can be used with each other.

Stylet 22 and cannula 24 are respectively fixed to parts of handle 26 so that stylet 22 and cannula 24 are axially slidable along each other with a close fit. By having a "close fit" and slidability, it is meant that there is no substantial separation or gap between members 22, 24, as by a boss or flange. Members 22 and 24 have a close and slidable fit along their respective distal portions, and in some embodiments that close and slidable fit extends along all or substantially all of their lengths.

Handle 26 has two rounded finger-holds or grips 80, a plunger 82, and a central opening through which members 22 and 24 extend, and in which an internal spring-loaded firing mechanism (not shown) is connected to plunger 82. An example of handle 26 that may be used in needle 20 is that currently used with QUICK-CORE® products sold by Cook Medical (Bloomington, Ind.). Embodiments of suitable handles are shown in U.S. Provisional Application No. 61/261,857, filed on Nov. 17, 2009, the entirety of which is incorporated herein by reference. Handle 26 is fixed to each of members 22 and 24 at their respective proximal portions. Members 22 and 24 are not rotatable with respect to each other or handle 26 around the longitudinal axis in the illustrated embodiments. Plunger 82 is used to cock the firing mechanism, prime needle 20 by moving stylet 22 along the longitudinal axis of needle 20 with respect to cannula 24, and to fire external member 24 forward from the cocked condition. The handle 26 permits a cocking step in which the firing mechanism for propelling cannula 24 is prepared, an insertion step in which needle 20 is inserted into the patient to a desired location, a priming step in which the inner member 22 is extended from outer member 24 (as indicated in FIG. 2) within or into the tissue of interest so that tissue can recoil or prolapse into space 34 via one or both of openings 44 and 46, and a firing step in which the firing mechanism is released to drive cannula 24 forward rapidly over stylet 22, so that sharpened distal end 64 rapidly traverses openings 44, 46 and thereby severs the tissue captured in space 34 from the surrounding tissue. The cocking step is performed by holding finger grips 80 and pulling back on plunger 82. In particular embodiments, during cocking stylet 22 and cannula 24 move together to maintain a relative position in which tip 33 of stylet 22 and end 64 of cannula 24 are together or adjacent each other. Once cocked, needle 20 can be inserted into the patient so that tip 33 and end 64 are in or almost in the tissue of interest. Extending stylet 22 from cannula 24 is accomplished while holding finger grips 80 by moving plunger 82 forward until plunger 82 reaches a stop or catch in the cocking mechanism. In the illustrated embodiments, all of space 34 moves out of cannula 24 during this priming step, and tissue recoils or prolapses to enter space 34 as it moves through the tissue. Firing cannula 24 is then accomplished by pushing forward plunger 82 to overcome the resistance of the cocking mechanism's stop or catch, and may be accomplished by the same hand that holds finger grips 80.

Cannula 24 and stylet 22 are slidable with respect to each other, as indicated above. Stylet 22 extends from its connection with handle 26 through the lumen 66 of cannula 24. In a particular embodiment, the outer diameter of stylet 22 is approximately the same as the inner diameter of cannula 24, so that cannula 24 supports stylet 22 along its length with little play or space between them, yet they can move smoothly with respect to each other.

As suggested above, stylet 22 and cannula 24 have a first relative position prior to pushing stylet 22 out of cannula 24, or after firing needle 20. In that first relative position (not shown), the respective ends 32 and 64 of stylet 22 and cannula 24 are substantially coextensive, with at most tip 33 or a part of it extending from the end 64 of cannula 24. Both openings 44 and 46 to space 34 are covered by cannula 24 in that first relative position. When stylet 22 is moved forward relative to cannula 24 (or cannula 24 is withdrawn relative to stylet 22) from that first relative position in a priming step, members 22 and 24 have a second relative position that corresponds to a pre-fired state of needle 20 (e.g. FIG. 2). In that second relative position, all or at least part of both openings 44 and 46 to space 34 are uncovered by cannula 24. As previously noted, the illustrated embodiments of needle 20 have the entirety of openings 44 and 46 becoming uncovered (i.e. the entirety of space 34 is exposed) when needle 20 is primed by moving stylet forward with respect to cannula 24.

While in the illustrated embodiments, the entirety of openings 44, 46 are shown uncovered by outer member 24 when the members 22, 24 are in their second relative position, needle 20 may be configured such that in the second relative position, a portion of opening 44 and/or 46 remains covered by outer member 24. For example, with respect to FIG. 3, rather than having proximal portion 31 of inner member 22 extending outside outer member 24, proximal portion 31 of inner member 22 may remain within outer member 24 when the members 22, 24 are in their second relative positions. It is also contemplated that more of stylet 22 than merely the portion having space 34 may extend from cannula 24 in the priming step, especially if stylet 22 is hollow. In that case, as more of stylet 22 is extended into tissue, more tissue can enter space 34 and extend into the lumen of hollow stylet 22.

The use of needle 20 will now be described in the context of obtaining a sample of soft tissue for testing purposes. It will be understood that methods for obtaining samples of other tissues or for other purposes are also contemplated. For example, embodiments of needle 20 could also be used through an endoscope, such as for obtaining gastrointestinal, urological, or bronchial sample(s) via the working channel of an endoscope.

The surgeon or other medical professional first determines a location in a patient, with its depth under the skin, from which a tissue sample is desired. Handle 26 is cocked so that, in one embodiment, members 22 and 24 are in the first relative position indicated above, with openings 44, 46 to space 34 covered by cannula 24. In that state, the medical professional places the distal end of needle 20 against the skin at a place proximate to the desired location, and inserts needle 20 at a desired angle or orientation and to a desired depth. Distal ends 32 and 64 force a path through the skin and subcutaneous tissue to a point in or just before the tissue or location from which a sample is to be taken. Insertion in this way, with end 32 and tip 33 of stylet 22 filling or slightly extended from end 64 of cannula 24, results in little or no tissue being forced into lumen 66 of cannula 24 as end 32 of stylet 22 pushes tissue outward slightly in front of cannula 24.

The clinician may take one or more images (e.g. x-ray, CT scan, etc.) to monitor or determine the placement of needle 20. When needle 20 is located as the clinician desires, with tip 33 or another part of distal end 32 in or adjacent to the tissue to be sampled, it is primed by moving plunger 82 forward (distally) to extend stylet 22 from the end of cannula 24 as indicated above. Through such extension, tissue space 34 is exposed from cannula 24. As stylet 22 penetrates through the tissue and some or all of space 34 is exposed, tissue recoils or prolapses through one or both of openings 44, 46 and into space 34. Edges along struts 36, 38 can guide or cut tissue into or toward space 34 as stylet 22 moves forward.

When stylet 22 has been extended as desired and the tissue sample rests in space 34, needle 20 is fired. Pressing plunger 82 forward from the primed position releases or overcomes a catch in handle 26, allowing a spring in handle 26 to shoot cannula 24 forward (distally) over stylet 22. Cutting end 64 of cannula 24 cuts a profile through tissue as it moves over openings 44, 46, thereby severing the tissue within space 34 from the surrounding tissue. The captured tissue is maintained within space 34, surrounded by struts 36, 38 and the internal wall of cannula 24.

Needle 20 is then carefully withdrawn from the patient, and once needle 20 has been withdrawn from the body, the tissue sample is removed from needle 20. Removal may be accomplished by first exposing space 34 and openings 44, 46, as by repeating the cocking and priming actions noted above, over a container for the tissue. The tissue may simply fall out of space 34 through one or the other of openings 44, 46. In embodiments having one opening (e.g. opening 44) larger than the other, a tissue sample may more easily fall out of or be extracted from larger opening 44, as such an opening may subtend an arc of greater than 180 degrees and so struts 36, 38 will not reach both ends of a diameter of the tissue sample within space 34. The presence of plural openings (e.g. the two openings 44, 46) prevent or limit any partial vacuum between the tissue and stylet 22, making removal or extraction of a full sample easier. If necessary, tissue can be extracted from space 34 by tapping needle 20, or by poking or applying pressure to the tissue through one of the openings (e.g. opening 46, if smaller) until it falls out from space 34 into a receptacle.

The ease of removal of tissue samples allows not only uncomplicated use by the physician, analyst or other professional, but it also facilitates the acquisition of multiple, relatively large samples with the same needle 20. Once a first sample is taken, needle 20 is easily unloaded and readied to take another sample, from the same location or a different location in the patient. Where some existing full core devices require involved steps to extract tissue, embodiments of needle 20 can be used once, the full or near-full core sample can be dropped, tapped or pushed out, and needle 20 readied (e.g. recocked) for reuse. Therefore, the time and effort needed to acquire a number of relatively large tissue samples for analysis can be reduced.

Internal and external members 22, 24 may be made of any of a variety of rigid biocompatible materials, or others that will not spoil or taint the tissue sample, such as stainless steel or nitinol. Other embodiments may use appropriately sturdy flexible materials for at least part of one or both of the members, although it will be understood that performance may suffer if such flexible materials tend to buckle or otherwise do not permit easy advancement of internal member 22 or external member 24. In particular embodiments, one or both openings 44, 46 may have a standard length, such as 10 millimeters or 20 millimeters, or may have lengths determined by patient need or usefulness in a particular part of the body.

It will also be understood that needle 20 may be placed through another access device (not shown) that is in, adjacent or on the way to a tissue area to be sampled. For example, an outer needle or sheath (not shown) may be inserted percutaneously through the skin, subdermal tissue, and/or other tissues, with needle 20 being inserted through the outer needle or sheath. Operation of needle 20 as indicated above, with needle 20 being advanced through additional tissue if needed, can then take place.

As noted above, in some embodiments stylet 22 and cannula 24 are non-rotatable with respect to each other. In this way, the orientation of the cutting portions (e.g. edges 70, 70a, 70b) of cannula 24 with respect to openings 44, 46 of stylet 22 is maintained. It is also contemplated that members 22 and 24 may be connected with handle 26 so that they are rotatable with respect to each other. For example, external member 24 may be rotated around a stationary internal member 22. Of course, it will be seen that both members may be rotatable at least to a degree, or cannula 24 may be stationary as stylet 22 turns inside it. Embodiments in which one or both of members 22, 24 are rotatable with respect to each other and/or to handle 26 may operate identically or substantially as discussed above.

It has been observed that longer throw-length notched partial-core biopsy needles can sometimes bend or buckle in certain situations. As the notch is made longer, to accommodate more tissue, there is a reduction in the amount of force required to bend the thin structure of the notch area. The dual struts 36, 38 of the present embodiments provide a thin structure, so as to obtain a full or near-full core sample, yet provide complementary strength to limit or prevent bending. Bending forces generally directed perpendicular to openings 44, 46 (generally vertically as viewed in FIG. 2), which are of particular concern with some partial-core needles, are countered by the structure and placement of struts 36, 38. Further, forces that may be generally directed parallel to openings 44, 46 (generally into or out of the page as viewed in FIG. 2) must overcome not one but two structures in order to bend. That is, a force generally directed to the side of strut 36 must overcome not only the stiffness of strut 36, but also the stiffness of strut 38 and the rigid connection of the struts to the rest of stylet 22.

Inner member 22 (e.g. in FIG. 2) may be formed by taking a hollow cannula of a suitable material, such as stainless steel or nitinol, and grinding or machining away portions corresponding to openings 42, 44, such as by wire electrical discharge machining (EDM). Distal portion 30 may then be filled with a suitable solid material that can be sharpened and/or crimped or closed to form end or tip 33. Proximal portion 31 of member 22 may also be wholly or partially filled with solid material, if desired, or it may be unfilled, in which case a lumen would extend throughout all or substantially all of proximal portion 31 from openings 42, 44 to handle 26. As indicated, such a hollow embodiment permits the proximal portion 31 of inner member or stylet 22 to cut tissue and accommodate cut tissue within the lumen of the stylet. In this way, tissue can enter a portion of stylet 22 proximal of space 34 prior to firing needle 20. A sample larger than space 34 can thus be obtained.

Inner member 22 may be alternatively be prepared as or machined from a solid rod, such as by wire EDM. Space 34, with openings 44 and 46 and/or other features noted above, are cut or machined into the rod. Use of a solid rod or wire so prepared can provide a greater degree of crush-resistance along the portion of stylet 22 proximal of space 34, which can be valuable if needle 20 is used in sturdier (e.g. cartilaginous or bony) tissue.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected. It is to be understood that structures or embodiments described in one context or with respect to one component may be used in other contexts or with respect to other components.

What is claimed is:

1. A biopsy needle, comprising:
   an external tubular member having an internal lumen and a sharpened distal end;
   an internal member defining a central longitudinal axis and having a proximal portion connected to a distal portion, said distal portion including first and second spaced apart struts along a sample-containment space through which the axis extends and a tissue penetrating tip, said first strut having first and second edges adjoining a first surface facing the axis and said second strut having third and fourth edges adjoining a second surface facing the axis, said first and second surfaces forming a boundary of said sample-containment space, said sample-containment space having first and second radially-opposed lateral openings wherein the first lateral opening is bounded by the first and third longitudinal edges and the second lateral opening is bounded by the second and fourth longitudinal edges; and
   wherein said internal member is slidably positioned within said lumen of said external member between a first relative position in which said sample-containment space and lateral openings are at least partially extended from said external member, and a second relative position in which said sample-containment space and lateral openings are entirely within said lumen.

2. The biopsy needle of claim 1, wherein said first and second surfaces are concave.

3. The biopsy needle of claim 2, wherein said concave surfaces are uniform along the respective lengths of said first and second struts, and each form a portion of a cylinder centered on said central longitudinal axis.

4. The biopsy needle of claim 1, wherein said tissue penetrating tip is in a longitudinal plane defined by said first and second struts.

5. The biopsy needle of claim 1, wherein said first and second openings have approximately the same length measured along said longitudinal axis.

6. The biopsy needle of claim 1, wherein said first opening has a larger length measured along said longitudinal axis than said second opening.

7. The biopsy needle of claim 6, wherein said first opening subtends an arc of the perimeter of said inner member that is more than 180 degrees.

8. The biopsy needle of claim 7, wherein said arc is approximately 200 degrees.

9. The biopsy needle of claim 8, wherein a plane defined by the middles of said first and second struts is offset from said longitudinal axis.

10. The biopsy needle of claim 1, wherein said distal portion of said inner member includes first and second end surfaces bounding said space, said end surfaces contacting each of said struts and being oblique to said longitudinal axis.

11. The biopsy needle of claim 10, wherein said first and second end surfaces are substantially planar across a diameter of said internal member.

12. The biopsy needle of claim 10, wherein said first and second end surfaces point toward each other, so that said first and second radially-opposed lateral openings have different lengths and/or different widths.

13. The biopsy needle of claim 1, wherein said inner member is a tubular member having an inner diameter, and said first and second surfaces are part of said inner diameter of said tubular member.

14. The biopsy needle of claim 1, wherein said inner member is a solid non-hollow member, so that the portions of said inner member adjacent said sample-containment space are filled in.

15. The biopsy needle of claim 1, wherein said external member defines an inner circumference and an outer circumference and first and second cutting edges for cutting across the first and second side openings respectively.

16. The biopsy needle of claim 1, wherein the sample-containing space is unobstructed so that a sample may be removed from said space by passing through either of said first and second lateral openings.

17. The biopsy needle of claim 1, wherein at least one of said edges can guide tissue past such edge and into said sample-containing space.

* * * * *